（12）United States Patent
McCarty, III

(10) Patent No.: US 10,080,646 B2
(45) Date of Patent: Sep. 25, 2018

(54) TENDON FIXATION DEVICE

(71) Applicant: L. Pearce McCarty, III, Orono, MN (US)

(72) Inventor: L. Pearce McCarty, III, Orono, MN (US)

( * ) Notice: Subject to any disclaimer, the term of this patent is extended or adjusted under 35 U.S.C. 154(b) by 256 days.

(21) Appl. No.: 14/701,799

(22) Filed: May 1, 2015

(65) Prior Publication Data
US 2016/0317282 A1    Nov. 3, 2016

(51) Int. Cl.
*A61F 2/08*    (2006.01)
*A61B 17/56*   (2006.01)

(52) U.S. Cl.
CPC ..... *A61F 2/0811* (2013.01); *A61F 2002/0858* (2013.01); *A61F 2002/0888* (2013.01)

(58) Field of Classification Search
CPC ........................................................ A61F 2/08
USPC .... 623/13.11–13.16; 606/151, 289, 300–321
See application file for complete search history.

(56) References Cited

U.S. PATENT DOCUMENTS

| | | |
|---|---|---|
| 5,632,748 A | 5/1997 | Beck, Jr. et al. |
| 5,702,397 A | 12/1997 | Goble et al. |
| 6,379,361 B1 | 4/2002 | Beck, Jr. et al. |
| 7,468,074 B2 | 12/2008 | Caborn et al. |
| 7,572,283 B1 | 8/2009 | Meridew |
| 8,048,158 B2 | 11/2011 | Hays |
| 8,512,405 B2 | 8/2013 | Baird |
| 8,790,368 B2 | 7/2014 | Sullivan et al. |
| 8,845,725 B2 | 9/2014 | Barwood et al. |
| 2004/0068262 A1* | 4/2004 | Lemos .................. A61F 2/0811 424/426 |
| 2006/0095130 A1 | 5/2006 | Caborn et al. |
| 2009/0287259 A1 | 11/2009 | Trenhaile et al. |
| 2010/0069958 A1 | 3/2010 | Sullivan et al. |
| 2011/0106252 A1 | 5/2011 | Barwood et al. |
| 2011/0112558 A1 | 5/2011 | Whayne et al. |
| 2013/0006278 A1* | 1/2013 | Mayer .................. A61B 17/686 606/151 |
| 2013/0261677 A1* | 10/2013 | Bouduban ............. A61F 2/0811 606/323 |
| 2015/0032157 A1 | 1/2015 | Dooney, Jr. et al. |

FOREIGN PATENT DOCUMENTS

EP    2486856    7/2014

OTHER PUBLICATIONS

Notification of Transmittal of the International Search Report and the Written Opinion of the International Searching Authority, or the Declaration, dated Aug. 8, 2016.

\* cited by examiner

*Primary Examiner* — Yashita Sharma
(74) *Attorney, Agent, or Firm* — Fish & Richardson P.C.

(57) ABSTRACT

Anchoring a tendon to a bone is achieved by forming a tunnel in the bone and employing a self-anchoring integrally formed anchor body. A portion of the tendon is wrapped around the anchor body and then the anchor body is driven into the tunnel to attach the tendon to the bone.

17 Claims, 5 Drawing Sheets

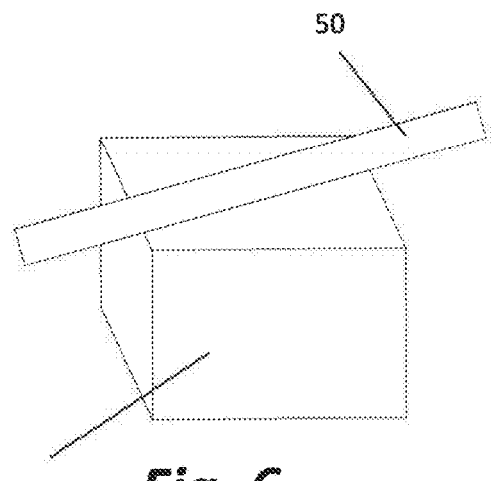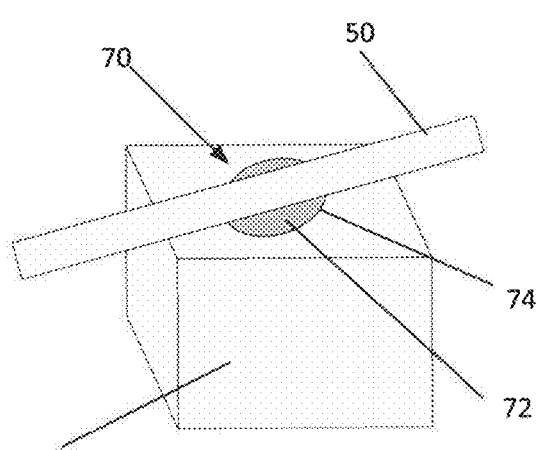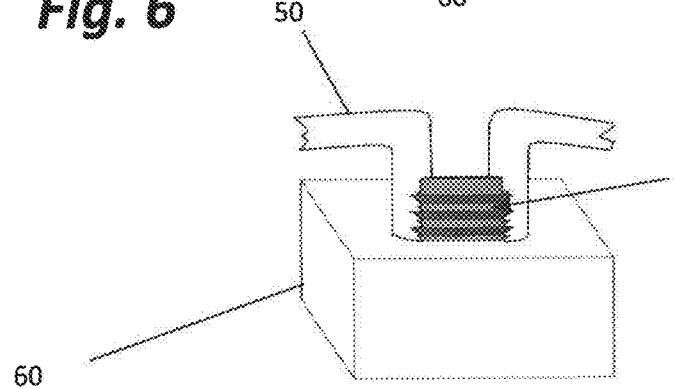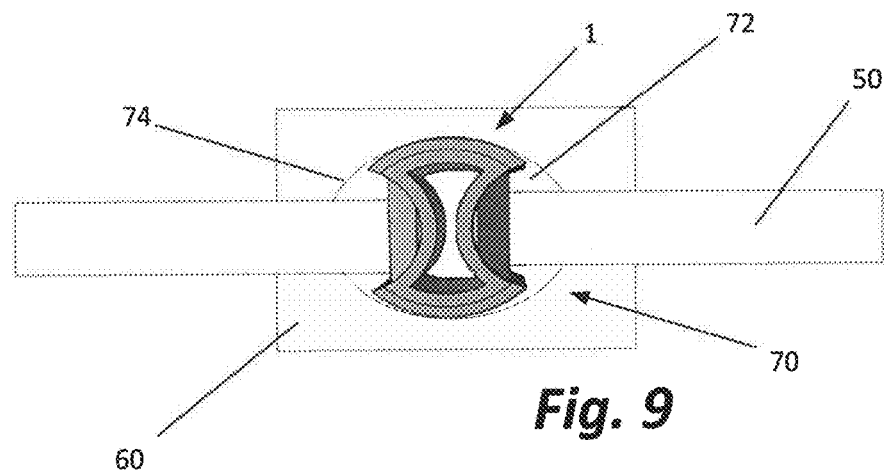

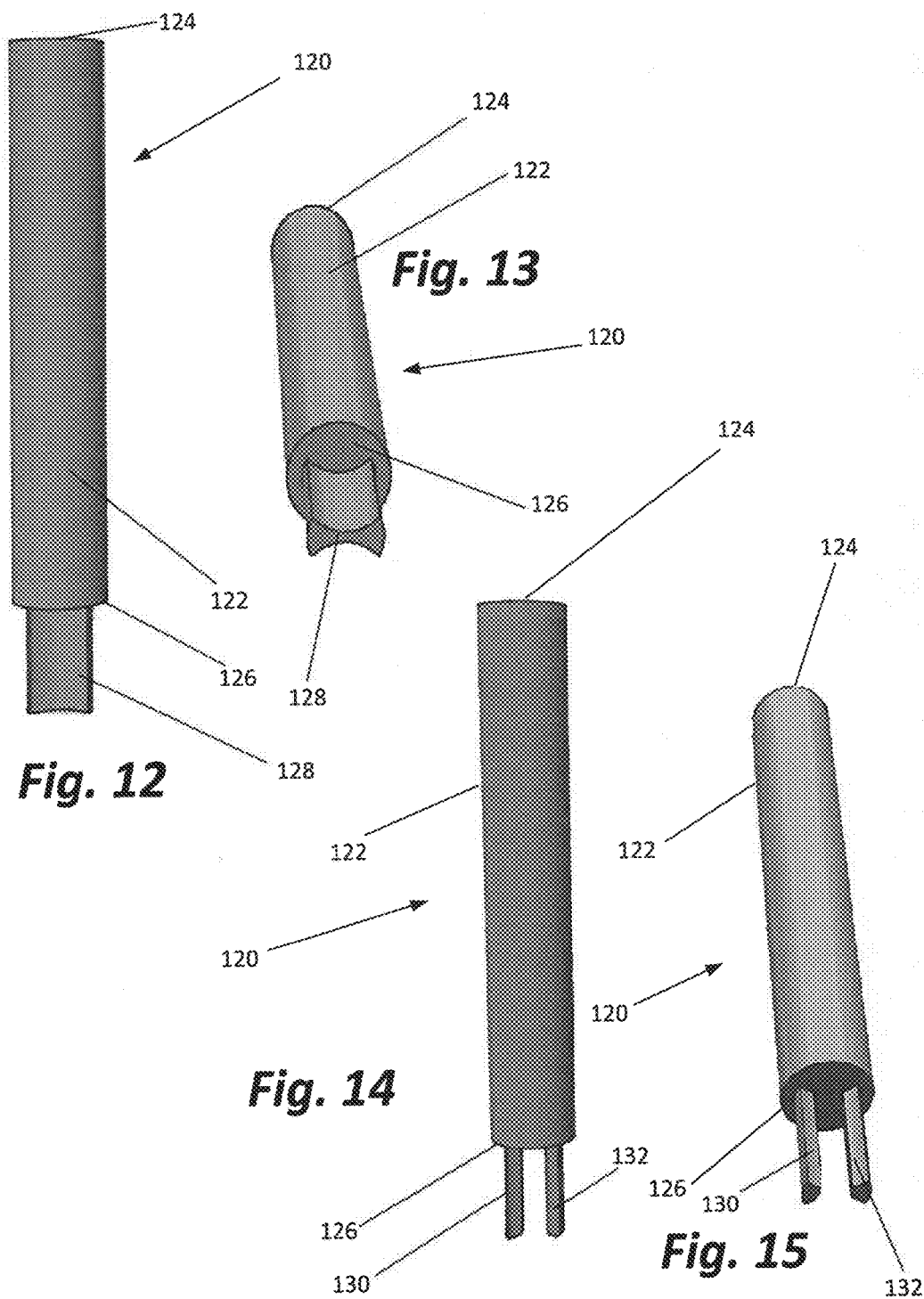

TENDON FIXATION DEVICE

CROSS-REFERENCED TO RELATED APPLICATIONS

Not applicable.

STATEMENT REGARDING FEDERALLY SPONSORED RESEARCH OR DEVELOPMENT

Not applicable.

BACKGROUND OF THE INVENTION

I. Field of the Invention

The present invention relates to surgical implants used in orthopedic surgery. More specifically, this invention relates to devices used to attach a tendon to a bone.

II. Related Art

A variety of different implantable devices have been employed to achieve tendon fixation to bone without the necessity of sutures or other secondary fixation intermediaries. The devices are generally used in the context of tendon repair or "tenodesis" surgery. In the case of the former, the device is used to reattach a tendon that has avulsed from its attachment. In the latter, the device is used to attach or fix a tendon in a given location that achieves a specific therapeutic end for the patient. For example, in the case of a "biceps tenodesis" procedure, most commonly the long head of the biceps tendon is fixed to bone in either a proximal location within the bicipital groove or in a more distal location in order to reduce or eliminate pain coming from a damaged portion of the tendon.

U.S. Pat. No 5,632,748 granted May 27, 1997 to Beck, Jr. et al discloses several different anchor devices. Each includes an anchor body and a separate threaded insertion member that is used either to wedge the anchor body against the wall of a tunnel formed in the bone, or to expand the anchor body against the wall of the tunnel. Implanting multiple parts in a confined area is inherently difficult, particularly when one must also employ tools to hold the anchor body in a position so the anchor body will not unduly pinch the tendon being anchored and, at the same time, tools to insert the insertion member into the tunnel adjacent the anchor body or into the anchor body itself. It is also difficult to achieve proper purchase of such parts in the tunnel to secure the tendon in place.

U.S. Pat. No. 8,048,158 to Mays et al likewise shows anchor devices including a ligament engagement member disposed in a bone tunnel with the ligament alongside the engagement member, and a locking member also disposed in the tunnel and engaging the ligament engagement member to wedge the ligament engagement member and ligament against the wall of the bone tunnel. The devices shown in Hays et al suffer from the same deficiencies as those shown in the aforementioned Beck, Jr. et al patent.

U.S. Pat. No. 8,512,805 to Baird discloses an anchor which also has two different pieces that are wedged against each other and the wall of a tunnel formed in the bone to secure a tendon in place. The Baird patent also discloses a tool for inserting the two implants which include a sharp tip inserted through the tendon to hold it in place as the two implants are pounded into the tunnel and wedged against each other. While this may assist in implanting the two pieces of the implant and holding the tendon in place, proper purchase and damage to the tendon remains an issue.

SUMMARY OF THE INVENTION

Anchoring a tendon to a bone can be achieved by forming in the bone a tunnel having an opening and a circumferential wall and providing an integrally formed and self-anchoring anchor body. In one embodiments the anchor body has a first end and a second end. Extending between the two ends are a pair of opposing concave walls and a pair of opposing convex walls. The radii of curvature of the two opposing convex walls of the anchor body are such that they form two opposing arcs along a single circle. This design element permits a surgeon to drill or punch a single, circular socket (i.e., tunnel) for implantation of the anchor body.

The first end of the anchor body comprises a flat engagement surface. The fiat engagement surface engages a surface of an impaction tool during implantation of the anchor body. The second end of the anchor body comprises a concave engagement surface having arches at the bottom of the opposing concave walls. This second end engages a tendon to be secured by the anchor body, permitting direct control of the tendon as well as a measure of fixation during the implantation process. These arches extend between the convex walls.

The anchor body has two sets of ribs. The ribs of a first set project outwardly from each of the pair of opposing convex walls. These ribs are adapted to engage the circumferential wall of the tunnel formed in the bone such that their angles resist backing out of the device after implantation. The ribs of a second set project outwardly from each of the pair of opposing concave walls. These ribs are adapted to engage a tendon extending along these walls and their angles are such that they resist slippage of the given tendon against the body of the anchor.

The anchor body may also be provided with a central channel, extending through the anchor body, open to the first and second. One or more connecting members spanning the central channel between the two concave walls may also be provided. Such a connecting member serves to increase the structural rigidity of the anchor body depending upon the material out of which the anchor is manufactured and to provide a post around which a suture may be tied.

The overall length of the anchor body, as measured linearly from the first end to the second end, will vary depending on the anatomic location of use. For example, the implantation of the anchor body within the canal of the humerus will typically require a shorter anchor body than implantation within the proximal humerus. The diameter of the anchor body may vary for similar reasons.

When the above-described anchor body is employed, the tendon to be joined (or "tenodesed") to the hone is placed over the tunnel opening. The anchor body is then placed over the tendon and opening such that a portion of the tendon resides within the arches and engages the concave engagement surface. The anchor body is then inserted into the tunnel. As this occurs, portions of the tendon on opposing sides of the concave engagement surface are sandwiched between the circumferential wall of the tunnel and the two concave walls of the anchor body such that the ribs of the second set of ribs engage the tendon. At the same time, the ribs of the first set of ribs engage the circumferential wall of the tunnel to secure the anchor body and tendon to the bone.

Some surgeons may find holding the tendon and anchor body in the proper orientation is most easily achieved by employing a piece of suture material that extends down through the central channel of the anchor body, around the tendon and then back up through the channel, This piece of suture material may be used to pull the tendon into the arches and into contact with the concave engagement surface. The device may be equipped with a wire loop (or loops) that extends through the central, hollow portion of the anchor that would facilitate passage of such a piece of suture material through the body of the anchor. The suture may also be used to retain, at least temporarily, the tendon in contact with the concave engagement surface to simplify the process of inserting the anchor body and tendon into the tunnel formed in the bone. If use of a suture is desired and the anchor body is provided with the aforementioned connecting member spanning the gap (i.e., central channel) between the two concave walls of the anchor body, the surgeon may tie the suture to the connecting member. Doing so may also provide additional fixation of the tendon to the anchor body and potentially provide a further impediment to tendon slippage during or after fixation of the tendon to the bone using the anchor body.

An impaction tool having an elongate shaft, a flange and a tip may also be employed. The impaction tool is adapted to be coupled to the first end of the anchor body. Specifically, the tip is inserted into the channel until the flange engages the flat engagement surface. A mallet may then be used to pound on the shaft and drive the anchor body into the bone tunnel. The flange is designed to have a diameter larger than the opening of the bone tunnel fashioned to accept the anchor and tendon, providing a "positive stop" and preventing over-insertion of the anchor. When the suture material is employed as discussed above, the tolerances between the tip and channel and/or first engagement surface and flange may be such that sufficient pinching forces are applied to the suture material to hold the suture material in place so that the tendon properly engages the concave engagement surface as the anchor body is inserted into the tunnel formed in the bone to couple the tendon to the bone. After insertion of the anchor body into the bone, the suture material may be extracted, or tied as described above and cut flush with the surface of the bone.

BRIEF DESCRIPTION OF THE DRAWINGS

The foregoing features, objects and advantages of the invention will become apparent to those skilled in the art from the following detailed description and with reference to the following drawings in which like numerals and the several views refer to corresponding parts.

FIG. 6 is a perspective view showing a piece of bone and a tendon;

FIG. 7 is a perspective view of the bone and tendon of FIG. 5 with a tunnel formed in the bone;

FIG. 8 is a perspective view of the bone, tendon and tunnel of FIG. 6 and the anchor body of FIG. 1 partially inserted into the tunnel;

FIG. 9 is a top view of the components of FIG. 7 with the anchor body fully inserted into the bone;

FIG. 12 is a side view of a first impaction tool intended for use with the anchor body of FIG. 3;

FIG. 13 is a perspective view of the impaction tool of FIG. 12;

FIG. 14 is a side view of a second impaction tool intended for use with the anchor body of FIG. 4;

FIG. 15 is a perspective view of the impaction tool of FIG. 14; and

DETAILED DESCRIPTION

Figure 1:
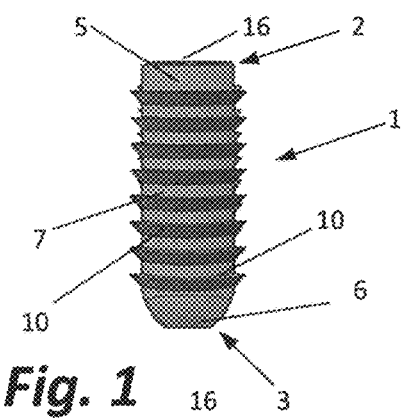
FIG. 1 is a front view of the anchor body of FIG. 1, the rear view being a mirror image thereof.
Figure 3:
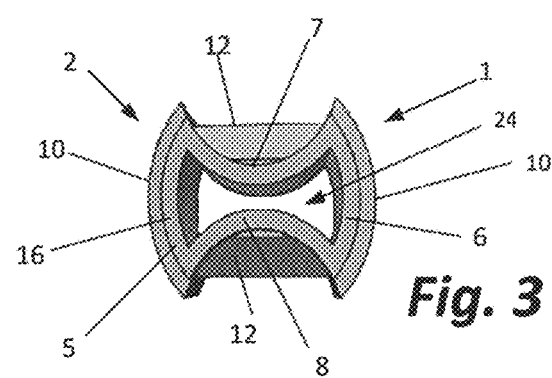
FIG. 3 is a top view of the anchor body of FIG. 1.
Figure 2:
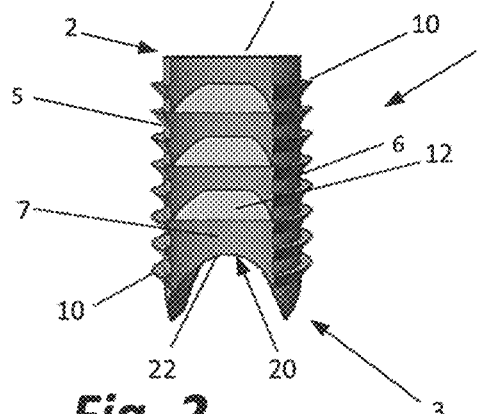
FIG. 2 is a side view of the anchor body of FIG. 1, the opposite side view being a mirror image thereof.

This description of the preferred embodiment is intended to be read in connection with the accompanying drawings, which are to be considered part of the entire written description of this invention. In the description, relative terms such as "lower", "upper", "horizontal", "vertical", "above", "below", "up", "down", "top" and "bottom", "under", as well as derivatives thereof (e.g., "horizontally", "downwardly", "upwardly", "underside", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "joined", and "joining" are used interchangeably and refer to one structure or surface being secured to another structure or surface or integrally fabricated in one piece unless expressly described otherwise.

FIGS. 1-4 show an integrally formed anchor body 1 having a first end 2 and a second end 3. Extending between the first end 2 and the second end 3 are a pair of opposing convex walls 5 and 6 and a pair of opposing concave walls 7 and 8. The radii of curvature of convex walls 5 and 6 are such that walls 5 and 6 form two opposing arcs of a single circle.

Projecting outwardly from each of the convex walls 5 and 6 are a first set of ribs 10. Eight such ribs 10 are illustrated on each of the convex walls 5 and 6. A fewer or larger number of ribs may be provided. Likewise, the shapes of the ribs 10 may be altered. Projecting outwardly from each of the concave walls 7 and 8 are a second set of ribs 12. Three such ribs 12 are illustrated on each of the concave side walls 7 and 8. Again, the number and shape of the ribs 12 may be varied.

Figure 4:
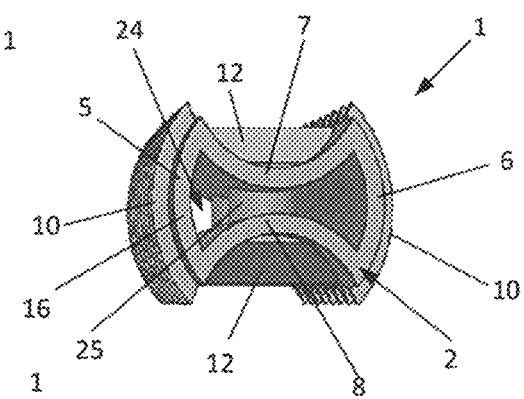
FIG. 4 is a top view of an alternative embodiment.

The first end 2 comprises a flat engagement surface 16. The second end 3 has a concave engagement surface 20. More specifically, the bottom of each concave wall 7 and 8 forms an arch 22 that extends between the bottoms of the two convex walls 5 and 6. A channel 24 extends through the center of anchor body 1. Channel 24 is surrounded by the walls 5, 6, 7 and 8 and is open to both the first end 2 and the second end 3. As illustrated in FIG. 4, this channel 24 may include one or more connecting members 25 dividing channel 24 in two. These connecting members 25 span the distance between the two concave walls 7 and 8 These connecting members 25 are integral with the remainder of anchor body 1. The connecting members 25 may be molded with the other portions of the anchor body 1 or the two ends of the connecting members 25 may be bonded or otherwise permanently attached to the inside surfaces of the concave walls 7 and 8.

FIGS. 5-9 illustrate how the anchor body is employed to couple a tendon 50 to a bone 60. First, and as shown in FIG. 6, the tendon 50 is placed proximate to a bone 60 to determine the desired attachment point. Next, and as shown in FIG. 7, a tunnel 70 is formed in the bone 60 at the attachment point. The tunnel 70 has an opening 72 and a circumferential wall 74. As shown in FIG. 8, after tunnel 70 has been formed, a portion of the tendon 50 is placed over the open end 72 of tunnel 70. The tunnel 70 may be a single, circular socket drilled or punched into the bone 60 if the convex walls 5 and 6 form two opposing arcs of a single circle, as described above. An anchor body 1 is then placed so that the second end 3 is in contact with the tendon 50. More specifically, the tendon 50 extends through the area beneath arches 22 between the bottoms of convex walls 5 and 6 and is in contact with the concave engagement surface 20. Finally, the anchor body 1 is driven into the tunnel 70 to reach the position shown in FIG. 9 and FIG. 5.

Figure 5:
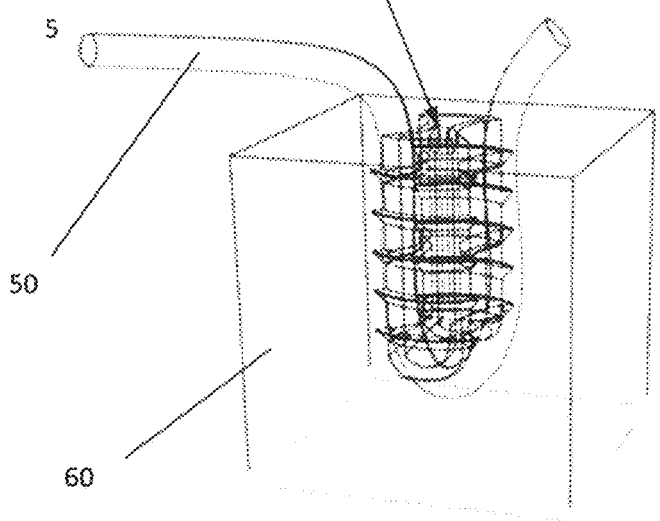
FIG. 5 is a perspective view of the anchor body of FIG. 1 being used to join a tendon to a bone.

FIG. 5 illustrates how the anchor body 1 and the circumferential wall 74 of tunnel 70 cooperate to anchor the tendon 50 to the bone 60. As shown, tendon 50 extends down along concave wall 7, under the concave engagement surface 20 (i.e., through the arches 22 at the bottom of the concave walls 7 and 8) and up along the concave wall 8. As such, tendon 50 is sandwiched between the circumferential wall 74 (and bottom) of tunnel. 70 and the two concave walls 7 and 8. The ribs 12 extending outwardly from the concave walls 7 and 8 engage the tendon 50 to hold the tendon 50 in place and prevent the tendon 50 from pulling out of the tunnel 70. The ribs 10 projecting from the convex walls 5 and 6 engage the circumferential wall 74 of the tunnel 70 to hold the anchor body 1 in place. As such, the integrally formed anchor body 1 is also self-anchoring since, once the anchor body 1 has been inserted into the tunnel 20, no other mechanical device, bonding agent or other mechanism is required to hold the anchor body 1 in place.

As noted above, the anchor body 1 may be provided with a central channel 24 open to the first end 2 and the second end 3. FIGS. 10-16 are provided to illustrate the functionality provided by such a channel 24.

Figure 10:
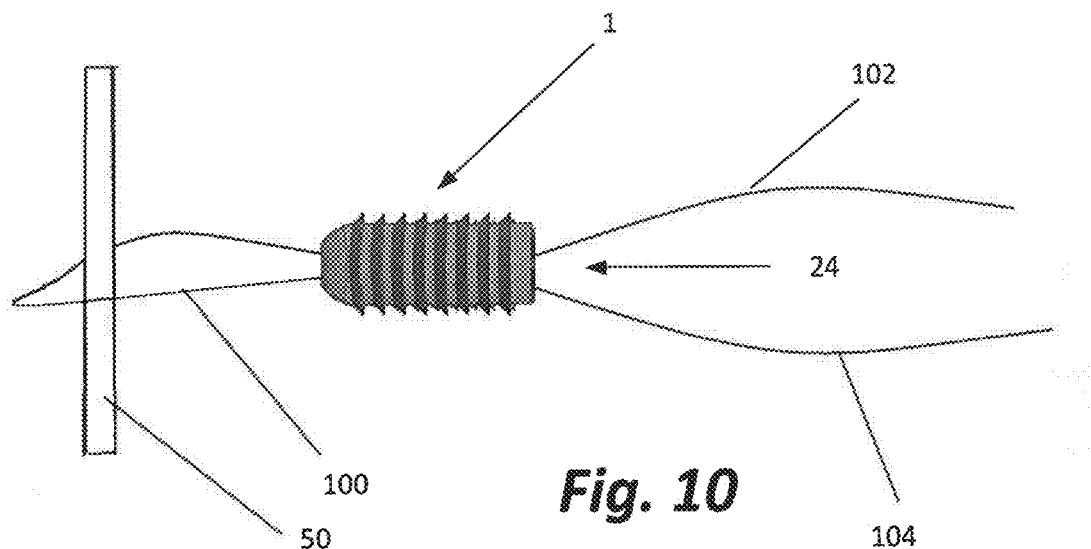
FIG. 10 illustrates a piece of suture material extending through the anchor body of FIG. 1 and around a tendon.

FIG. 10 shows a length of suture material 100 extending around a tendon 50. The two ends 102 and 104 of the suture material 100 have been fed through the central channel 24 of anchor body 1. Pulling on the free ends 102 and 104 of suture material 100 while holding he anchor body 1 serves to draw the tendon toward the anchor body 1. in FIG. 11, the suture material 100 is being used to secure the tendon into contact with the concave engagement surface 20. More specifically, the tendon 50 is in contact with arches 22 and is between the bottoms of the convex walls 5 and 6.

When the embodiment illustrated in FIG. 4 is employed, the connecting member(s) 25 not only provide internal support so the anchor body 1 does not collapse during insertion, thereby improving the compressive force directing the tendon against bone, the connecting member(s) 25 also provide a post over which the suture 100 can be tied to provide additional fixation of the tendon 50 to the anchor body 1 to help impede tendon slippage at least during implantation and potentially also after implantation.

Figure 11:
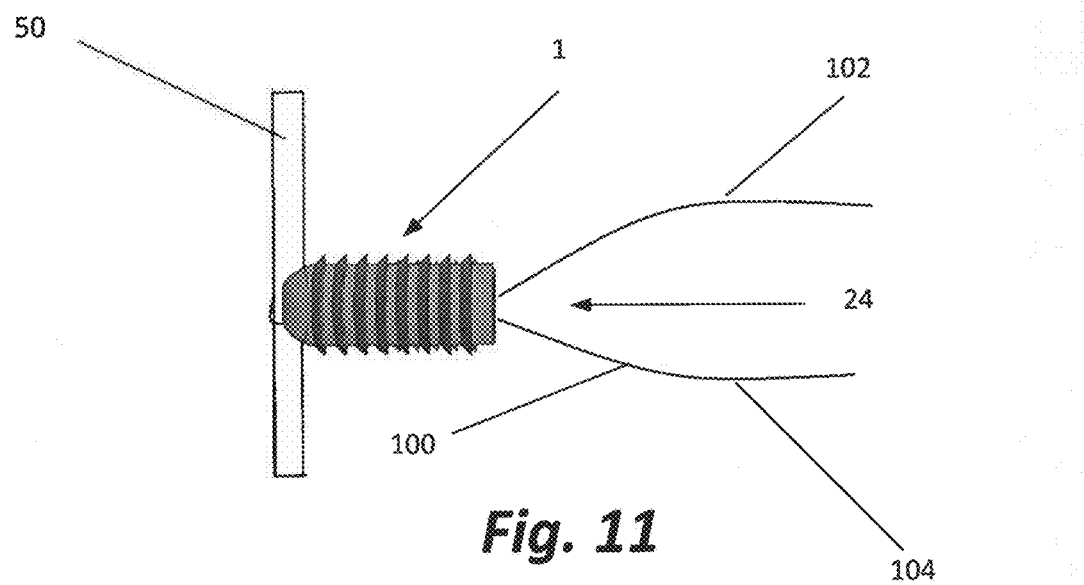
FIG. 11 illustrates an assembly comprising the components of FIG. 9, but with the tendon pulled tight against the anchor body.
Figure 16:
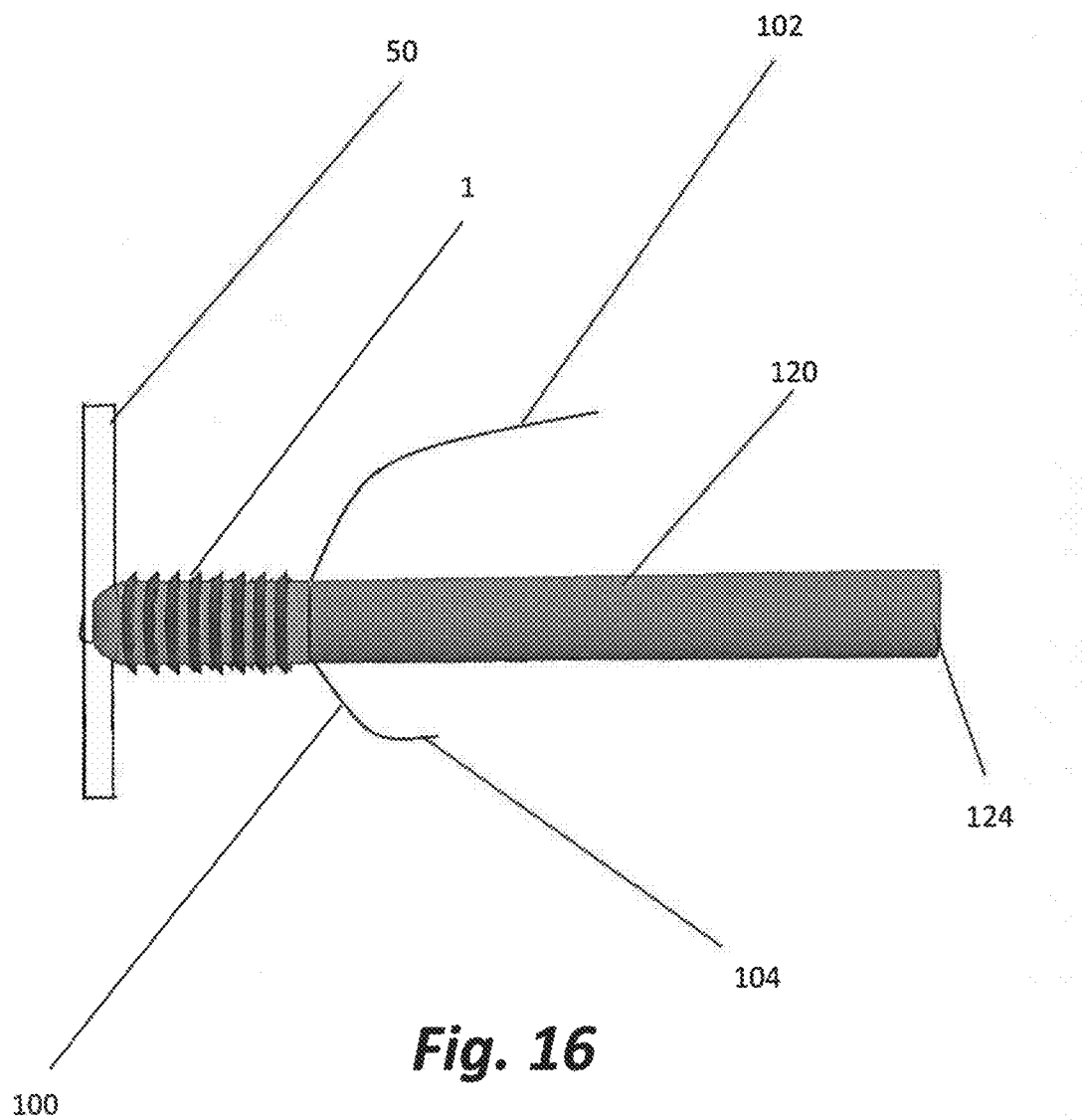
FIG. 16 shows an impaction tool coupled to an anchor body.

As shown in FIGS. 12 through 16, an impaction tool 120 may be provided. FIGS. 12 and 13 show an impaction tool 120 which is well suited for implantation of the anchor body shown in FIG. 3. FIGS. 14 and 15 show an impaction tool 120 well suited for implanting an anchor body 1 having inner connecting members 25, as shown in FIG. 4. Many features are shared by the impaction tool shown in FIGS. 12 and 13 and the impaction tool shown in FIGS. 14 and 15. Each comprises an elongate shaft 122 having a first end 124. A flange 126 is adjacent a second end of shaft 122. Projecting from the flange 126 approximately 180° from the shaft 122 is a tip. The embodiment of FIGS. 12 and 13 has a tip comprising a single member 128. The size and shape of the tip 128 are adapted to permit the tip 128 to be inserted into the channel 24, shown in FIG. 3, until the flange 126 contacts the flat engagement surface 16 of the first end 2 of anchor body 1. The fit between the tip 128 and the surfaces defining channel 24 is intended to be snug. As such, there is enough pinching force exerted between the tip 128 and the surfaces defining channel 24 to hold the suture material 100 and the tendon in engagement with the concave engagement surface 20, as shown in FIG. 11. The embodiment of FIGS. 14 and 15 differs only in that the tip has two members 130 and 132. These members 130 and 132 reside on opposite sides of connecting member(s) 25 when the tool and anchor member are coupled together.

From the foregoing, one skilled in the art will appreciate no more than two hands are required to (i) wrap the suture material 100 around the tendon 50 and pass the free ends 102 and 104 of the suture material 100 through the channel 24 of anchor body 1; (ii) draw and then hold the tendon 50 in proper engagement with the concave engagement surface 20; (iii) insert the tip (128 in FIGS. 12 and 13 and 130/132 in FIGS. 14 and 15) of the impaction tool 120 into the channel 24 of anchor body 1 until the flange 126 reaches the flat engagement surface 16 to thereby temporarily secure the tendon 50, anchor body 1 and tool 120 together; (iv) use the tool 120 to insert the tendon 50 and second end 3 of anchor body 1 into the tunnel 70; and (v) tap on the end 124 of the tool 120 with a mallet (not shown) to drive the anchor body and attached tendon 50 into the tunnel 70 to couple the tendon 50 to the bone 60. The procedure is then completed by retracting the tool 120 from the channel 24 (and the surgical site) and trimming the suture material. As such, the disclosed embodiment may be employed to secure a tendon to a bone either in traditional open fashion, or arthroscopically.

From the foregoing, one of ordinary skill should also recognize that various modifications may be made without deviating from the invention. For example, the anchor body may be made from any number of biocompatible materials. Some examples include poly ether ether ketone (PEEK) and similar plastics, poly-L-lactic acid (PLLA)and similar bioabsorbable or biocomposite materials, titanium and various stainless steel alloys. Further, various materials could be employed instead of suture material to draw and hold the tendon in contact with the anchor body.

For example, a strap of shape memory material such as nitinol could be extended between the bottoms of the two convex walls around the tendon. The nitinol material, as it is warmed from room temperature (about 68° F.) its body temperature (about 98.6° F.) would reach its transition temperature and then change shape to draw the tendon into contact with the concave engagement surface. This would eliminate the need for the channel. Further, the tool could be designed with a socket to receive the first end of the anchor body rather than a tip inserted into the anchor body. As previously noted, the number of ribs extending from the concave and convex walls may be altered. The shape of the ribs may also be altered. The dimensions of the concave and convex walls and concave recess may be altered to accommodate tendons and bones of differing thicknesses. The dimensions of the bone anchor 1 may also be adapted for use at different implantation sites.

The foregoing description is intended to explain the various features and advantages, but is not intended to be limiting. The scope of the invention is defined by the following claims which are also intended to cover a reasonable range of equivalents.

What is claimed is:

1. A method for coupling a tendon to a bone comprising:
   a. forming a tunnel in a bone, said tunnel having an opening and a circumferential wall;
   b. providing a self-anchoring integrally formed anchor body having a first end, a second end, a pair of opposing concave walls and a pair of opposing convex walls extending between the first and second ends, a flat engagement surface at the first end, a concave engagement surface comprising arches in the opposing concave walls extending between the convex walls at the second end, a first set of ribs projecting outwardly from each of the pair of opposing convex walls and adapted to engage the circumferential wall formed in the bone, a second set of ribs projecting outwardly from each of the pair of opposing concave walls and adapted to engage a tendon, the anchor body further comprising a channel extending through the anchor body from the first end to the second end, the anchor body further comprising at least one connecting member spanning the channel between the opposing concave walls;
   c. placing a tendon over the opening of the tunnel;
   d. placing the anchor body over the opening of the tunnel such that a portion of the tendon resides between the convex walls and in the arches of the opposing concave walls; and
   e. impacting the anchor body into the tunnel so that the ribs of the first set of ribs projecting from each of the convex walls engage the circumferential wall of the tunnel to secure the anchor body in place in the tunnel and the ribs of the second set of ribs projecting from each of the concave walls engage portions of the tendon sandwiched between the concave walls and the circumferential wall of the tunnel to secure the tendon to the anchor body.

2. The method of claim 1 further including the steps of providing a piece of suture material having two ends, extending the suture material around the tendon and the ends through the channel, and then employing the suture material to hold a portion of the tendon between the convex walls and in the arches of the opposing concave walls.

3. The method of claim 1 further including the step of providing a tool having a tip and flange, inserting the tip into the channel until the flange comes into contact with the flat engagement surface such that the suture material is pinched between the insertion tool and the anchor body.

4. The method of claim 1 further including the steps of providing a piece of suture material and tying the tendon to the connecting member of the anchor body using the piece of suture material.

5. The method of claim 3, wherein the tip of the tool consists of a single member.

6. The method of claim 3, wherein the tip of the tool comprises at least two members.

7. The method of claim 1, wherein the anchor body is made of a material selected from a group consisting of polyether ether ketone, poly-L-lactic acid, titanium, stainless steel, and combinations thereof.

8. The method of claim 1, wherein the pair of opposing convex walls of the anchor body form two opposing arcs along a single circle.

9. A method for coupling a tendon to a bone comprising:
   forming a tunnel in a bone, the tunnel having an opening and a wall;
   positioning a tendon over the opening of the tunnel;
   positioning an anchor body over the opening of the tunnel, the anchor body comprising a first end, a second end, at least one concave wall and at least one convex wall extending between the first and second end, a flat engagement surface at the first end, an arched portion at the second end, a first set of ribs projecting outwardly from the convex wall, a second set of ribs projecting outwardly from the concave wall, the anchor body further comprising a channel that extends through at least a portion of the anchor body and is open to the first end, wherein the anchor body further comprising at least one connecting member spanning the channel;
   contacting a portion of the tendon with the second end of the anchor body; and
   impacting the anchor body into the tunnel such that the first set of ribs projecting from the convex wall engages the wall of the tunnel to secure the anchor body in place in the tunnel and the second set of ribs projecting from the concave wall engages portions of the tendon sandwiched between the concave wall and the wall of the tunnel to secure the tendon to the anchor body.

10. The method of claim 9, wherein the contacting comprises engaging a portion of the tendon with a concave engagement surface of the second end of the anchor body.

11. The method of claim 10, wherein the concave engagement surface comprises an arch adapted for engaging the tendon.

12. The method of claim 9, further comprising extending a portion of a suture around a portion of the tendon and extending a portion of the suture through the channel to secure the tendon to the second end of the anchor body.

13. The method of claim 9, further comprising engaging a tool having a tip and flange with the first end of the anchor body, and using the tool to insert the tendon and the second end of anchor body into the bone.

14. The method of claim 13, wherein the first end of the anchor body comprises a flat engagement surface, and wherein the engagement of the tool and the anchor body comprises advancing the tip of the tool into the channel of the anchor body until the flange comes into contact with the flat engagement surface of the anchor body.

15. The method of claim 14, further comprising engaging the tool with a suture such that the suture is pinched between the flange of the insertion tool and the flat engagement surface of the anchor body.

16. The method of claim 15, further comprising retracting the tool from the channel and trimming the suture.

17. The method of claim 9, wherein the channel has a circular cross-section.

* * * * *